United States Patent [19]

Mott

[11] Patent Number: 5,507,765
[45] Date of Patent: Apr. 16, 1996

[54] PUNCH-TYPE SURGICAL INSTRUMENT FOR SKIN INCISION, SET OF PARTS FOR MAKING SUCH AN INSTRUMENT OF SELECTABLY VARIABLE SIZE, AND BLADE UNIT FOR SUCH INSTRUMENT

[76] Inventor: James B. Mott, 850 Central Ave., Ste. 200, Naples, Fla. 33940

[21] Appl. No.: 234,250

[22] Filed: Apr. 28, 1994

[51] Int. Cl.[6] .............................. A61B 17/14; A61B 1/00
[52] U.S. Cl. ........................................ 606/184; 128/754
[58] Field of Search ............................ 606/131–133, 606/184; 128/754, 753; 30/358, 51, 71, 73, 78, 85, 337, 340

[56] References Cited

U.S. PATENT DOCUMENTS

| 3,512,519 | 5/1970 | Hall | 606/184 X |
|---|---|---|---|
| 3,515,128 | 6/1970 | McEvoy | 606/184 X |
| 3,577,979 | 5/1971 | van der Gaast | 128/754 |
| 3,913,566 | 10/1975 | Lacey | 606/184 X |
| 3,949,747 | 4/1976 | Hevesy | 128/754 |
| 3,990,451 | 11/1976 | Gibbs | 606/174 |
| 4,163,446 | 8/1979 | Jamshidi | 128/754 |
| 4,262,676 | 4/1981 | Jamshidi | 128/754 X |
| 4,873,991 | 10/1989 | Skinner | 128/754 |
| 5,123,907 | 6/1992 | Romaine | 606/131 |
| 5,183,053 | 2/1993 | Yeh et al. | 128/754 |
| 5,341,816 | 8/1994 | Allen | 606/179 X |

*Primary Examiner*—Stephen C. Pellegrino
*Assistant Examiner*—Nancy Mulcare
*Attorney, Agent, or Firm*—McCormick, Paulding & Huber

[57] ABSTRACT

A punch-type surgical instrument for skin incision along a closed line, such as a substantially elliptical line, includes a handle, a blade unit and a means for attaching the handle to the blade unit in a way achieving high stability between the handle and blade unit and which nevertheless allows the two parts to be made as ones easily connectable to and disconnectable from one another. The blade unit may be made and furnished in different sizes to cause the instrument to be one selectably variable in size.

20 Claims, 3 Drawing Sheets

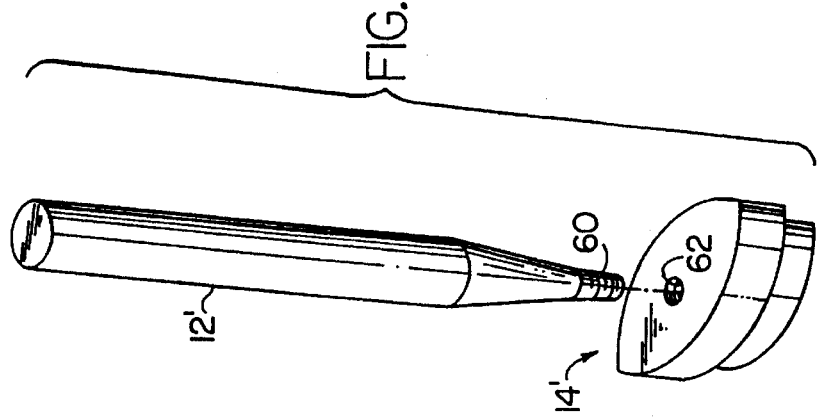
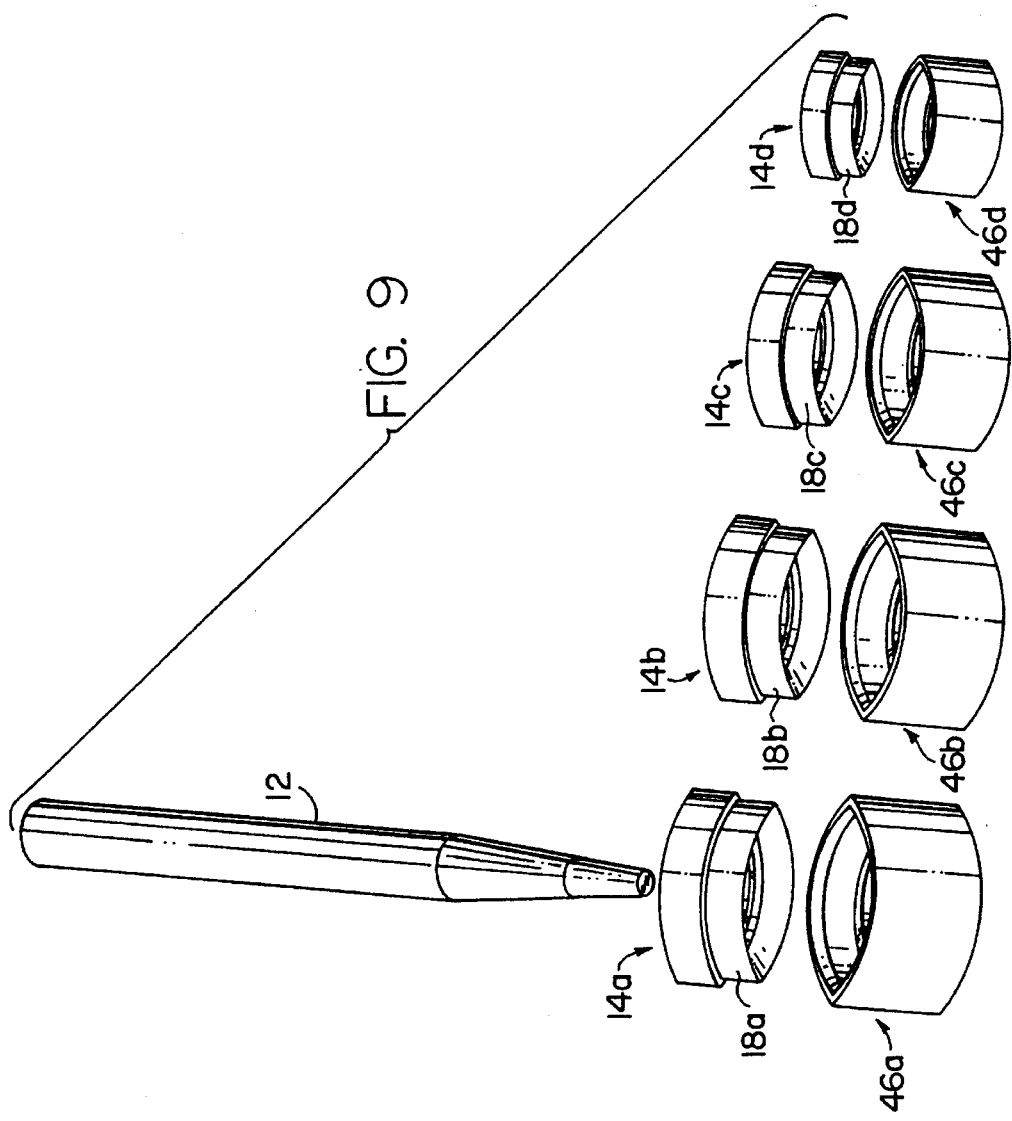

PUNCH-TYPE SURGICAL INSTRUMENT FOR SKIN INCISION, SET OF PARTS FOR MAKING SUCH AN INSTRUMENT OF SELECTABLY VARIABLE SIZE, AND BLADE UNIT FOR SUCH INSTRUMENT

FIELD OF THE INVENTION

The invention relates to a punch-type surgical instrument for incising skin in the process of taking a skin specimen for biopsy purposes or in removing a mole or other skin lesion and part or all of which instrument is disposable, and deals with an improvement in the construction of such instruments wherein the blade of the instrument is carried by and fixed to a plastic blade support member to form a blade unit capable of being stably fixed to an associated handle in a simple way to form the complete instrument.

BACKGROUND OF THE INVENTION

To remove a skin biopsy specimen or to remove a mole or other skin lesion it is known to incise the skin along a closed line completely penetrating the skin and to then remove the specimen or unwanted skin and tissue containing the lesion by further sharp and blunt dissection, and to thereafter perform a skin closure procedure. It is also known in the incision step to use punch-type instruments having sharp blades which accurately cut closed lines in the skin and which can be held and manipulated by one hand of the surgeon while his or her other hand is used to stretch the skin at the site of the incision. Exemplary ones of such instruments are disclosed in U.S. Pat. Nos. 1,577,979; 3,990,541; 5,123,907; and 5,183,053.

In making a skin incision of the type in question it is usually desirable to have it be of generally elliptical shape. Such an elliptical incision is important for achieving a more suitably appearing skin closure, and is especially beneficial if used while the skin is stretched and held in a cross-grain direction with respect to the skin lines of Langer while the incision is made. U.S. Pat. No. 5,183,053 shows a punch-type surgical instrument for cutting along a generally elliptical closed line, and U.S. Pat. No. 5,123,907 discusses the stretching of the skin relative to the skin's lines of Langer during the incision step.

If an attempt is made to make an elliptical incision free hand using a scalpel and by cutting at different times along two curved incisional lines defining the opposite sides of an ellipse, it is often difficult to make the two incisional lines perfectly symmetrical and therefore the subsequent skin closure, due to several factors, may be irregular. It is also difficult to properly evenly stretch the skin with respect to the lines of Langer while the incision is performed free hand. Therefore, the use of a punch-type instrument to avoid these problems is recommendable.

The amount of skin and adjacent tissue to be removed in the involved surgical procedure will vary from situation to situation, and therefore it is desirable that the punch-type instruments, if used, be available in different sizes so that in each procedure the surgeon will be able to make an incision of a size favorably suiting the biopsy specimen to be taken or lesion to be removed. Further, because of the nature of its use the instrument should be one which is of relatively inexpensive construction so that it can be used once and then be disposed of.

The general object of the invention is therefore to provide a punch-type instrument for skin incision which may be made with a blade having a generally elliptical shape, in which the blade is stably held relative to the handle to allow the blade to be moved by the handle in various directions without any looseness or slippage between the blade and handle, which can be easily made to cut incisions of different size, and which can be made of a sufficiently low cost as to render it suitably disposable after a single use.

SUMMARY OF THE INVENTION

The invention resides in a punch-type surgical instrument for skin incision with the instrument including a handle, a blade unit separate from the handle, and cooperating first means on the handle and second means on the blade unit for stably securing the handle to the blade unit, the blade unit including a metallic blade made as a tubular member surrounding an enclosed space and having an annular cutting edge and a plastic blade support member fixed to the blade and having a cross or platform portion extending across the space enclosed by the blade, the first connecting means of the blade unit being carried by and fixed relative to the cross or platform portion of the blade support member.

The invention also resides in the connecting means on the handle and the connecting means on the blade support member being such that the handle may be easily manually removed from and attached to the blade unit, and resides still further in the details of the construction of such connecting means on the cross portion of the blade support member and on the handle.

The invention still further resides in a set of parts from which an instrument having selectably variable size may be made, such set of parts including a handle and a plurality of blade units of different size each of which blade units is adapted to be manually connected to and removable from the handle.

The invention also resides in the combination with the blade unit of a shield or a cap which releasably fits onto the blade unit to protect the blade and to prevent it from causing injury prior to its use.

The invention further resides in a blade unit by itself which may be made in various different sizes and/or shapes and which is easily manually attachable to a handle to form a complete instrument.

The invention also resides in further details and features as mentioned in the accompanying claims.

BRIEF DESCRIPTION OF THE DRAWINGS

FIG. 9 is a perspective view showing a set of parts from which an instrument similar to that of FIG. 1, and of selectably variable size, may be made.

FIG. 10 is a view similar to FIG. 3 but showing an alternate embodiment of the invention.

DETAILED DESCRIPTION OF THE PREFERRED EMBODIMENTS

Figure 1:
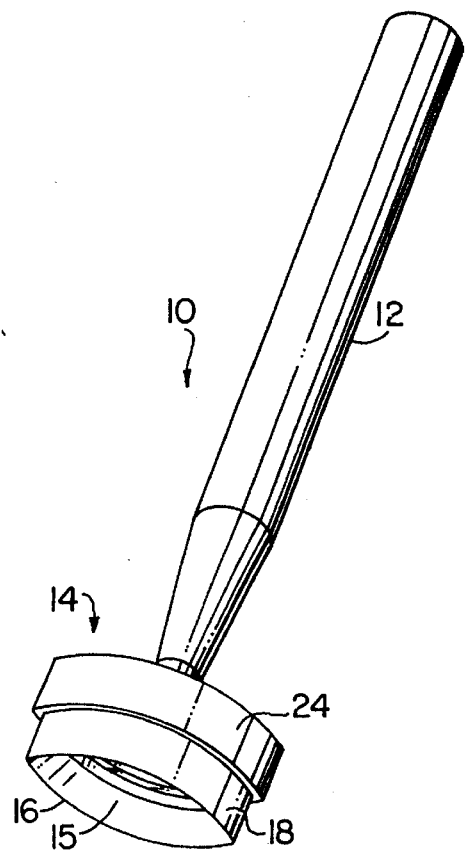
FIG. 1 is a perspective view of a punch-type surgical instrument for skin incision embodying the present invention.
Figure 2:
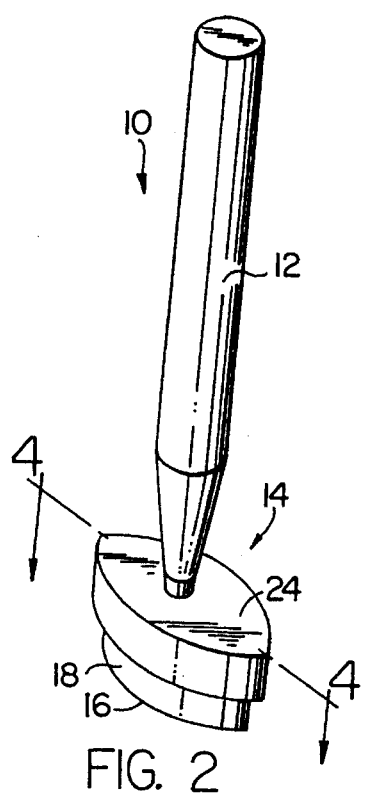
FIG. 2 is another perspective view of the instrument of FIG. 1.
Figure 3:
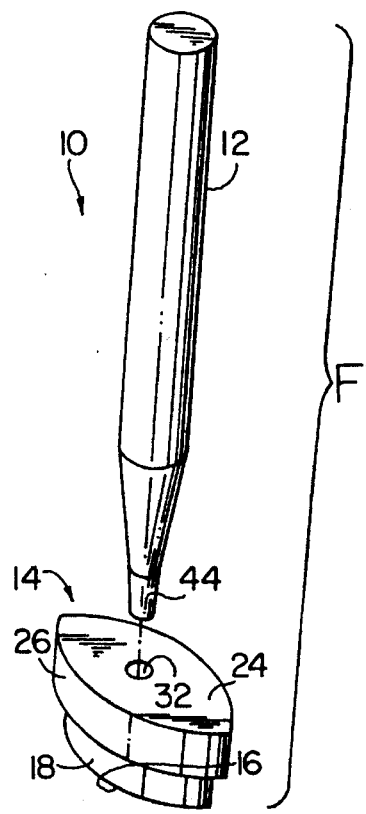
FIG. 3 is a view similar to FIG. 2 but showing the handle of the instrument removed from the blade unit.

Referring first to FIGS. 1, 2 and 3, a punch-type surgical instrument is illustrated generally at 10 and comprises basically an elongated handle 12, adapted to be held and manipulated by one hand of the surgeon, and a blade unit 14 providing a sharp cutting edge 16 extending along a closed annular line. The handle 12 may be made inexpensively as an injection molded part of a suitable plastic such as, for example, polypropylene. The shape defined by the cutting edge 16 may vary, however, it is preferably of a generally elliptical shape and is shown and described herein as having such shape. As shown in FIG. 3 the handle 12 and blade unit 14 are made as initially separate parts. If desired the finished instrument 10 may be made with the handle permanently secured to the blade unit so as to make it difficult or impossible to thereafter remove the blade unit from the handle.

Preferably, however, and as described in more detail hereinafter, the handle 12 and blade unit 14 are so constructed that the two parts are easily connectable and disconnectable relative to one another by simple manual operations so as to allow the parts to be furnished as separate items that can be assembled into the complete instrument 10 immediately prior to the use of the instrument. This has several advantages including: the separate parts may be easier to package and ship then completely assembled instruments; the handle may be reused if desired, with the blade unit being removed from the handle at the end of one procedure and with a new blade unit being attached to the handle at a later time for a subsequent procedure; and a plurality of blade units of different size may be provided and the handle may be attached to any one of such units to provide the instrument 10 as one having a selectably variable size.

Figure 4:
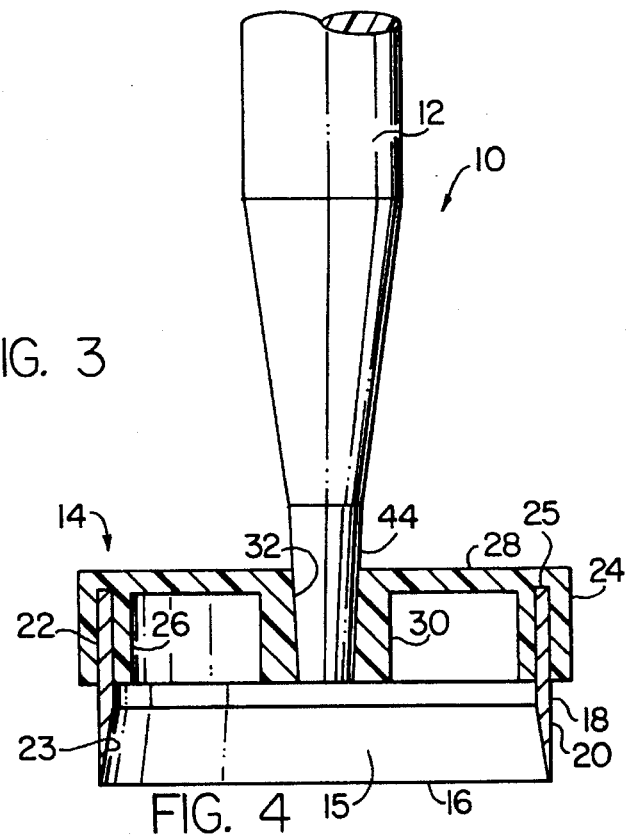
FIG. 4 is an enlarged fragmentary view of the instrument of FIG. 1 with the portion of the view relating to the blade unit being a cross-sectional view taken on the line 4—4 of FIG. 2.

The construction of the blade unit 14 is best shown in FIG. 4. As shown there, the unit 14 includes a metallic blade 18 made as a tubular body surrounding an enclosed space 15 and having a lower end portion 20 providing the lower annular cutting edge 16. The beveling of the blade to provide the sharpened edge 16 may be performed on either the inside or outside surface of the blade, and in the illustrated case is shown to have been done on the inside surface of the blade so as to describe the illustrated bevel surface 23. Extending upwardly from the lower portion 20 of the blade is an upper portion 22 housing an annular upper edge 25. A blade support member 24, made of any suitable plastic such as, for example, polypropylene, is rigidly fixed to and supports the upper blade portion 22. The blade support member 24 includes a peripheral or rim portion 26 which embeddedly receives the upper portion of the blade, and a cross or platform portion 28 extends across the space enclosed by the being located substantially in the plane of the upper edge 25 of the blade 18, the cross portion 28 forming essentially a top wall or cover for the blade unit. At the middle of the cross portion 28 it includes a protrusion 30 extending downwardly from its bottom side, with the protrusion providing in the cross portion 28 an opening 32 of substantial vertical length.

Figure 5:
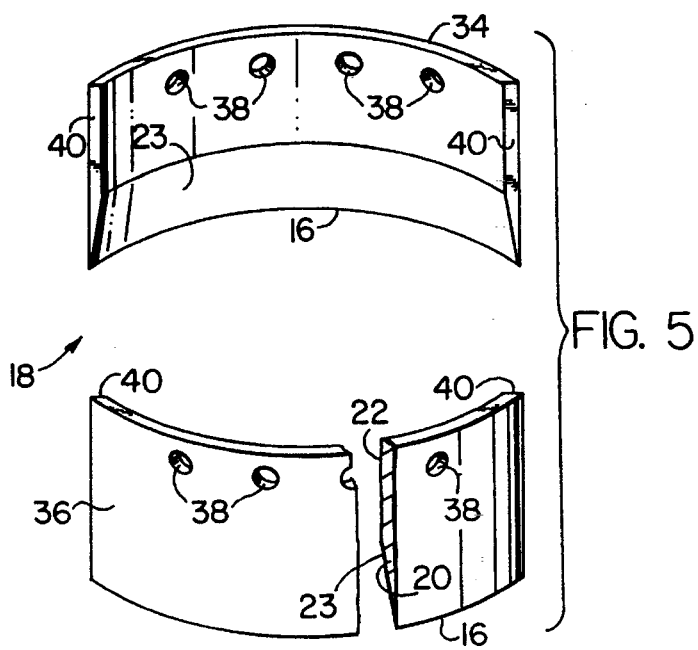
FIG. 5 is a perspective view showing the two initially separate pieces used in making the blade of the instrument of FIG. 1.
Figure 6:
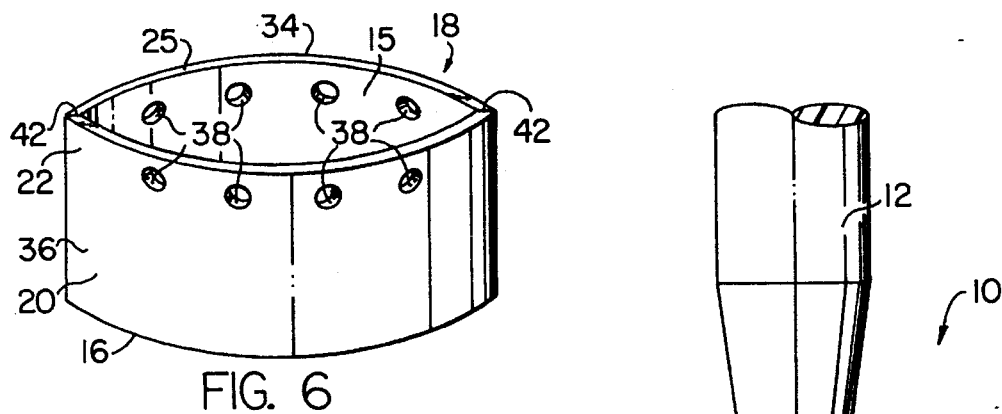
FIG. 6 is a perspective view showing the finished blade of the FIG. 1 instrument.

The blade 18 of the blade unit may be made in various different ways without departing from the broader aspects of the invention, but a preferred construction of it is shown in FIGS. 5 and 6. With reference to these figures, the blade 18 is made of two initially separate members 34 and 36 made as curved strips which are pre-sharpened and provided with holes 38 or similar locking features. The strips are or may be substantially identical to one another with each having two ends 40. In making the blade, the two strips 34 and 36 are placed as shown in FIG. 6 with their two pairs of two ends 40 abutting one another as shown. Then the two joints 42 appearing at the two locations of the abutting ends are welded, for example by means of a laser or electron beam welding process, to rigidly join the two strips 34 and 36 to one another to complete the finished tubular blade 18. This blade may then be placed into an injection plastic molding machine and by means of an insert molding process the blade support member 24 may be simultaneously made and attached to the blade. In this molding process the plastic material of the support member flows into and through the openings 38 of the blade 18 to aid in rigidly locking the blade to the support member.

In accordance with the invention, the handle 12 and the blade unit 14 are connected to one another by cooperable connecting means on the handle 12 and on the blade support member 24 of the blade unit 14. Referring to FIGS. 3 and 4 the connecting means on the handle 12 consists of an end portion 44 of the handle having a tapered frusto-conical shape, and the connecting means on the blade support member 24 of the blade unit 14 consists of the opening 32 which has a tapered frusto-conical shape matching that of the handle end portion 44. As seen looking down onto the top of the blade unit, the opening 32 is located at the middle of the cross portion 28 of the support member 24 and entirely within the space 15 enclosed by the blade 18. Further, the taper of the end portion 44 and of the opening 32 is a "locking" type taper, by which is meant one wherein the angle of taper is approximately one sixteenth of an inch per inch of length. That is, the diameter of the tapered end portion 44 of the handle increases in proceeding upwardly from the lower part of the tapered end portion at a rate of approximately one eighth inch per inch of upward movement.

Therefore, when the end portion 44 of the handle is inserted into the opening 32 of the blade unit 14, by using only a small amount of force and perhaps by twisting the handle slightly relative to the blade unit, a tight frictional attachment of the handle to the blade unit is obtained. The handle is stably held relative to the blade unit so that in use of the instrument the handle may be rocked or moved in any direction without any looseness occurring between it and the carried blade unit 14. Nevertheless, the attachment of the blade unit to the handle is also such that after use of the instrument the blade unit can be easily removed from the handle, if desired, by pulling the blade unit from the handle and by possibly twisting the handle relative to the blade unit as it is pulled. However, both the blade unit and the handle can be made as inexpensive parts, and if they are so made the entire instrument may, if desired, be disposed of after use without necessarily separating the blade unit from the handle.

It should also be noted that if it is desired to supply the instrument 10 with the blade unit 14 permanently attached to the handle 10 the same construction as illustrated in FIGS. 3 and 4 may be used with the end portion 44 of the handle being bonded to the blade support member 24 of the blade unit 14 through the use of an adhesive or a heat sealing process.

Figure 8:
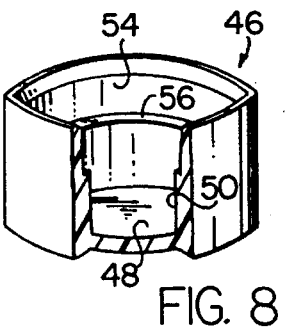
FIG. 8 is a perspective view, partly broken away, showing the shield of FIG. 7.
Figure 7:
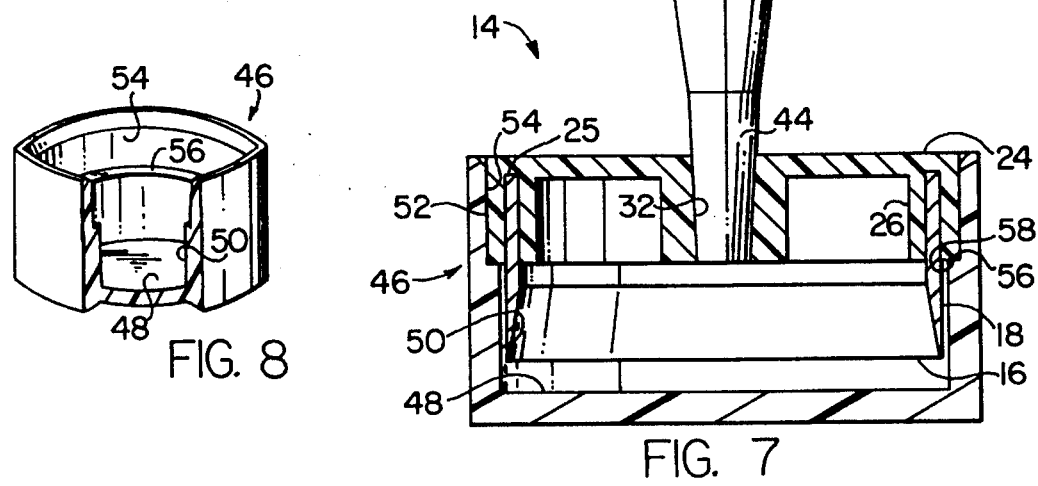
FIG. 7 is a view similar to FIG. 4 but showing the instrument with a shield assembled with the blade unit.

The blade units 14 are preferably provided with removable caps or shields to protect the blades of the units from damage and to prevent accidental cutting of persons handling the blade units prior to their actual use. Referring to FIGS. 7 and 8 a suitable cap or shield is illustrated there at 46 and, similar to the handle 12 and blade support member 24 of the blade unit 14, may be made as a molded plastic article using any suitable plastic, such as for example, polypropylene. FIG. 7 shows the shield 46 in its assembled position with respect to a blade unit 14, and FIG. 8 shows it removed from the blade unit.

The shield 46 has a bottom wall 48 and a side wall 50 extending upwardly from the bottom wall 48. In the assembled position of the shield the bottom wall 48 is spaced slightly below the sharpened edge 16 of the blade 18, and the side wall 50 the shield completely surrounds the blade 18. The blade support member 24 of the blade unit 14 has an exterior side surface 52, and in its upper portion 54 the side wall 50 of the shield has an interior side surface 54 of a shape complementary to that of the surface 52 and sized to frictionally slidably engage the surface of 52. At the lower end of the side surface 54 the side wall 50 of the shield has a shoulder 56 which abuttingly engages the downwardly facing surface of 58 of the peripheral portion 26 of the blade support member to limit movement of the shield onto the blade unit and to thereby prevent the bottom wall 48 from moving any closer to the sharpened edge 16 than as illustrated in FIG. 7. From a disassembled position, the shield 46 can be easily slid into assembled position with the blade unit 14 and it will frictionally retain such assembled position until it is later removed by manually sliding it from the blade unit. Preferably, the shield is not removed from the blade unit until the blade unit is assembled with the handle 12, the shield thereby facilitating the assembly process and preventing injury by the blade to the person performing the assembly.

As mentioned, the ability of the blade unit 14 to be easily manually attached to and removed from the handle 12 allows the parts to be supplied in such a way as to provide the surgeon with an instrument of selectably variable size. Such a feature is illustrated in FIG. 9 which shows a set of parts consisting of a single handle 12 and a plurality of blade units 14a, 14b, housing blades 18a, 18b, 18c, and 18 *d*, respectively 14c, and 14d and associated shields 46a, 46b, 46c, and 46d. Each of the blade units of 14a, 14b, 14c, and 14d are of the same construction as the blade unit 14 previously described and all have openings 32 (not shown in FIG. 9) of the same size so that any one of them can be attached to the handle 12 by inserting the end portion 44 of the handle into its opening 32. The blade units of 14a, 14b, 14c, and 14d, however, differ from one another by being of a different size with respect to their blades 18a, 18b, 18c and 18d as shown in FIG. 9. Therefore, in performing a procedure the surgeon may select from the plurality of blade units the one having the blade size best meeting his needs and may construct an instrument 10 by attaching that selected one of the blade units to the handle 12.

The shields of 46a, 46b, 46c, and 46d of FIG. 9 are likewise each identical in construction to the shield shown in FIGS. 7 and 8, but are of such different size from one another as to suitably fit onto their respectively associated blade units 14a, 14b, 14c, and 14d.

Other connecting means different from that described above may be used to connect the handle to a blade unit, and FIG. 10 shows another embodiment of the invention using another preferred construction of the connecting means. Referring to this figure the handle 12' and blade unit 14' are identical to the handle 12 and blade unit 14 previously described except for the means on the handle and on the blade unit for connecting the blade unit to the handle. As to this, the connecting means on the handle 12' comprises a threaded end portion 60 on the lower end of the handle, and the connecting means on the blade unit 14' comprises a complementary threaded opening 62 in the blade support member of blade unit 14'. Thereby the handle 12' may be attached to the blade unit 14' by threading its end portion 60 into the opening 62 of the blade unit; and thereafter the blade unit 14' can be removed from the handle by rotating the handle to unscrew its end portion 60 from the opening 62.

The invention claimed is:

1. A punch-type surgical instrument for skin incision, said instrument comprising:

a handle, a blade unit separate from said handle, and cooperating first connecting means on said handle and second connecting means on said blade unit for securing said handle to said blade unit, said blade unit including a tubular metallic blade surrounding an enclosed space, said blade having an annular lower portion defining an annular lower edge and also having an annular upper portion extending upwardly from said lower portion and defining an annular upper edge, said annular lower edge of said lower portion being sharpened for skin incising purposes, said blade unit also including a blade support member made of a plastic material fixed to said upper portion of said blade and having a cross portion extending across said enclosed space and located substantially in the plane of said upper edge of said tubular blade, said blade support member being fixed to said annular upper portion of said blade by said upper portion of said blade along its full annular extent being embedded in said plastic material of said blade support member, and said second connecting means being carried by and fixed relative to said cross portion of said blade support member so that as seen looking downwardly onto said blade unit said second connecting means is located at the middle of said cross portion of said blade support member and entirely within the space surrounded by said tubular blade.

2. A punch-type surgical instrument as defined in claim 1 further characterized by said blade support member including a rim portion surrounding said cross portion and extending downwardly from said cross portion, said upper portion of said blade being embedded in said rim portion with part of said rim portion being located on the exterior side of said blade upper portion and with annular part of said rim portion being located on the interior side of said blade upper portion.

3. A punch-type surgical instrument as defined in claim 1 further characterized by a shield movable into and out of an assembled position with respect to said blade unit, said shield having a bottom wall and a side wall extending upwardly from said bottom wall, said bottom wall when said shield is in said assembled position being spaced below said sharpened lower edge of said blade and said side wall surrounding said blade and abuttingly engaging said blade support member to prevent movement of said bottom wall any closer to said sharpened edge of said blade, said side wall of said shield having an interior side surface and said blade support member of said blade unit having an exterior side surface, which side surfaces slideably engage one another in said assembled position of said shield to frictionally hold said shield in said assembled position.

4. A punch-type surgical instrument as defined in claim 1 further characterized by said upper portion of said blade having openings passing therethrough and receiving some of said plastic material of said blade support member to firmly lock said blade to said blade support member.

5. A punch-type surgical instrument as defined in claim 4 further characterized by said blade being of elliptical shape in cross section and having two strip-like curved sides each having two ends and which strip-like sides are joined to one another at said ends to form said blade.

6. A punch-type surgical instrument as defined in claim 5 wherein said sides of said blade are initially separate from one another and are joined to one another at said ends by means of welding.

7. A punch-type surgical instrument as defined in claim 1 further characterized by said cross portion of said blade support member having a top surface and a bottom surface and having a protrusion located at the middle of said bottom surface and extending downwardly from said bottom surface, said second connecting means of said blade support member being an opening in said cross portion extending downwardly from said top surface into said protrusion.

8. A punch-type surgical instrument as defined in claim 7 further characterized by said handle being an elongated member, said first connecting means on said handle being an end portion of said handle having a tapered frusto-conical shape, and said opening in said cross portion of said blade support member being adapted to snugly receive said tapered end portion of said handle with a frictional force fit.

9. A punch-type surgical instrument as defined in claim 7 further characterized by said handle being an elongated member, said cooperating first connecting means on said handle being a threaded end portion of said handle, and said opening in said cross piece of said support member of said blade unit being threaded and sized to threadably mate with said threaded end portion of said handle.

10. A set of parts for making a punch-type surgical instrument of selectively variable size for skin incision, said set of parts comprising:

a handle, and a plurality of blade units separate from said handle, each of said blade units including a tubular metallic blade surrounding an enclosed space, said blade having an annular lower portion defining an annular lower edge and also having an annular upper portion extending upwardly from said lower portion and defining an annular upper edge, said annular lower edge of said blade being sharpened for skin incision purposes, and a plastic blade support member fixed to said upper portion of said blade and having a cross portion extending across said enclosed space above said lower edge of said blade and located substantially in the plane of said upper edge of said tubular blade, said blade support member of each of said blade units being fixed to said annular upper portion of said blade by said upper portion of said along its full annular extent being embedded in said plastic material of said blade support member, said blades of said plurality of blade units being of different sizes, said handle including a first connecting means, and each of said blade units including a second connecting means on said cross portion of its blade support member which second connecting means is so positioned that as seen looking downwardly onto said blade unit said second connecting means is located at the middle of said cross portion of said blade support member and entirely within the space surrounded by said tubular blade, and which second connecting means is cooperable with said first connecting means of said handle to permit said blade unit to be manually attached to and removed from said handle, whereby a complete instrument for making an incision of a selected size may be obtained by selecting one of said blade units from said plurality of blade units and attaching it to said handle.

11. A set of parts as defined in claim 10 further characterized by said handle being an elongated member, and said first connecting means on said handle being one end portion of said handle having a tapered frusto-conical shape, said cross portion of said blade support member of each of said blade units having a top surface and a bottom surface and having a protrusion located at the middle of said bottom surface and extending downwardly from said bottom surface, and said second connecting means on each of said blade units being an opening in said cross portion of said blade support member which opening extends downwardly from said top surface of said cross portion into said protrusion and is adapted to snugly receive said tapered end portion of said handle with a frictional force fit.

12. A set of parts as defined in claim 10 further characterized by said handle being an elongated member, said cooperating first connecting means on said handle being a threaded end portion of said handle, said cross portion of said blade support member of each of said blade units having a top surface and a bottom surface and having a protrusion located at the middle of said bottom surface and extending downwardly from said bottom surface, and said second cooperating means on each of said blade units being a threaded opening in said cross piece of said support member of said blade unit which opening extends downwardly from said top surface of said cross portion into said protrusion and is threaded and sized to threadably mate with said threaded end portion of said handle.

13. A set of parts as defined in claim 10 further characterized by said blade support member of each of said blade units including a rim portion surrounding said cross portion and extending downwardly from said cross portion, said upper portion of said blade being embedded in said rim portion with part of said rim portion being located on the exterior side of said blade upper portion and with another part of said rim portion being located on the interior side of said blade upper portion, and said upper portion of said blade having openings passing therethrough and receiving some of said plastic material of said blade support member to firmly lock said blade to said blade support member.

14. A set of parts as defined in claim 10 further characterized by a plurality of shields each associated with a respective one of said plurality of blade units, each of said shields being moveable into and out of an assembled position with respect to its associated blade unit, and each of said shields having a bottom wall and a side wall extending upwardly from said bottom wall, said bottom wall when said shield is in said assembled position with respect to its associated blade unit is spaced below said sharpened lower edge of said blade and said side wall surrounding said blade and abuttingly engaging said blade support member to prevent movement of said bottom wall any closer to said sharpened edge of said blade said side wall of each of said shields having an interior side surface and said blade support member of the associated one of said blade units having an exterior side surface, which side surfaces slideably frictionally engage one another in said assembled position of said shield to frictionally hold said shield in said assemble position with respect to its associated blade unit.

15. A blade unit for use with an associated handle having a first connecting means to form a punch-type surgical instrument for skin incision, said blade unit comprising:

a tubular metallic blade having an annular lower portion defining an annular lower edge and also having an annular upper portion extending upwardly from said lower portion and defining an annular upper edge, said lower edge of said blade being sharpened for skin incision purposes, said tubular blade surrounding an enclosed space, a plastic blade support member fixed to said upper portion of said blade and having a cross portion extending across said enclosed space above said sharpened lower edge of said blade and located substantially in the plane of said upper edge of said tubular blade, and second connecting means carried by said cross portion of said blade support member for cooperation with said first connecting means of said handle to enable said blade unit to be manually attached to and removed from said handle, said second connecting means being so positioned on said cross portion that, as seen looking downwardly onto said blade unit, said second connecting means is located at the middle of said cross portion of said blade support member and entirely within the space surrounded by said tubular blade.

16. A blade unit as defined in claim 15 further characterized by said cross portion of said blade support member having a top surface and a bottom surface and having a protrusion located at the middle of said bottom surface and extending downwardly from said bottom surface, said second connecting means of said blade support member being an opening in said cross portion extending downwardly from said top surface into said protrusion.

17. A blade unit as defined in claim 16 further characterized by said blade being of generally elliptical shape and having two strip-like curved sides each having two ends, and said strip-like sides being joined to one another at said ends to form said tubular blade.

18. A blade unit as defined in claim 16 wherein said sides of said blade are initially separate from one another and are joined to one another at said ends by means of welding.

19. A blade unit as defined in claim 15 in combination with a shield movable into and out of an assembled position with respect to said blade unit, said shield having a bottom wall and a side wall extending upwardly from said bottom wall, said bottom wall when said shield is in said assembled position being spaced below said sharpened lower edge of said blade and said side wall surrounding said blade and abuttingly engaging said blade support member to prevent movement of said bottom wall any closer to said sharpened edge of said blade.

20. The combination defined in claim 19 further characterized by said side wall of said shield having an interior side surface and said blade support member of said blade unit having an exterior side surface, which side surfaces slidably frictionally engage one another in said assembled position of said shield to frictionally hold said shield in said assembled position with respect to said blade unit.

* * * * *